United States Patent [19]
Okorodudu

[11] Patent Number: 4,859,356
[45] Date of Patent: Aug. 22, 1989

[54] N,N-DIORGANODITHIOCARBAMATE-ALKYLTHIOSULFINYL HALIDE REACTION PRODUCTS AND LUBRICANT COMPOSITIONS CONTAINING SAME

[75] Inventor: Abraham O. M. Okorodudu, West Deptford, N.J.

[73] Assignee: Mobil Oil Corporation, New York, N.Y.

[21] Appl. No.: 236,405

[22] Filed: Aug. 24, 1988

[51] Int. Cl.[4] ........................................ C10M 135/18
[52] U.S. Cl. .................................. 252/47.5; 560/302; 560/310
[58] Field of Search ................ 252/47.5; 560/302, 310

[56] References Cited

U.S. PATENT DOCUMENTS 2,690,440  9/1954  Himel et al. .................... 560/302
2,927,131  3/1960  Louthan ......................... 560/302
3,015,670  1/1962  Wolff ............................ 560/310

Primary Examiner—William R. Dixon, Jr.
Assistant Examiner—Jerry D. Johnson
Attorney, Agent, or Firm—Alexander J. McKillop; Charles J. Speciale; Michael J. Mlotkowski

[57] ABSTRACT

Disclosed are products derived from the reaction of amine or metal salts of N,N-diorganodithiocarbamic acids with alkylthiosulfinyl halides. These compositions are useful as antioxidants and antiwear additives in lubricating oil compositions.

16 Claims, No Drawings

N,N-DIORGANODITHIOCARBAMATE-ALKYL-THIOSULFINYL HALIDE REACTION PRODUCTS AND LUBRICANT COMPOSITIONS CONTAINING SAME

FIELD OF THE INVENTION

This invention relates to the novel compounds resulting when alkylthiosulfinyl halides are reacted with the amine or metal salts of N,N-diorganodithiocarbamic acids. In another aspect this invention relates to lubricant compositions containing these compounds.

DISCUSSION OF THE PRIOR ART

Metal salts of dithiocarbamic acid have been known an additives for lubricating oils. U.S. Pat. No. 4,226,733 discloses the use of nickel alkyldithiocarbamates as additives to prevent ultra-violet degradation of lube oils. U.S. Pat. No. 4,428,861 discloses sulfidation reactions of dialkyl dithiocarbamates.

SUMMARY OF THE INVENTION

In one aspect this invention comprises the reaction product resulting from the reaction of an alkylthiosulfinyl halide and a N,N-diorganodithiocarbamate salt. In another aspect this invention comprises the lubricant composition containing the afore-described reaction product and a lubricating oil.

DESCRIPTION OF THE INVENTION

Representative of the amine or metal dithiocarbamate salts are those having the following structure

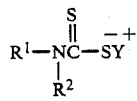

where $R^1$ and $R^2$ are the same or different. $R^1$ and $R^2$ are each a hydrocarbyl group containing from 1 to 36 carbon atoms, having none or at least one heteroatom which can be oxygen, sulfur, or nitrogen. $R^1$ and $R^2$ are selected from alkyl, alkenyl, aryl, aralkyl, alkaryl groups and can contain phenyl, naphthyl, or anthryl substituents; $R^1$ and $R^2$ can be a $(CH_n)_m$ group comprising part of an alicyclic or heterocyclic system selected from, for example, pyrrole, pyrrolidine, piperidine, morpholine etc. where n is 1 or 2 and m is 2 to 8. Y is an ammonium or metal radical.

A preferred dithiocarbamate salt is the triethylammonium salt of N,N-di-2-ethylhexyl-dithiocarbamic acid. This salt is prepared by reacting bis-2-ethylhexyl amine and carbon disulfide in the presence of triethylamine in toluene.

Other preferred metal or amine salts include the amine or metal salts of other diorganodithiocarbamic acids derived from other secondary amines, for example, dialkyl, aryl alkyl, diaryl, dialkylaryl, diarylalkyl, alkyl arylalkyl, arylalicyclic, or heterocyclic amines, reacted in the presence of suitable aprotic solvents such as toluene, benzene or hexane. Other suitable metals salts include the sodium or potassium salts of N,N-diorganodithiocarbamic acids prepared by reacting a secondary amine with carbon disulfide in the presence of sodium, or potassium hydroxide in toluene.

The alkyl thiosulfinyl halides have the structural formula:

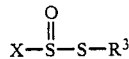

where X is halogen, preferably chlorine and $R^3$ is an aryl, alkaryl, aralkyl, or saturated or unsaturated alkyl substituent of 1 to 36 carbon atoms in number. The alkyl thiosulfinyl halide compounds are prepared by reacting an alkyl, aryl, alkylaryl, or arylalkyl thiol with a thionyl halide such as thionyl chloride, $SOCl_2$. Preferred thiols include: butyl, nonyl, dodecyl and benzene thiols.

The alkyl thiosulfinyl compound and the ammonium or metal dithiocarbamate salt are reacted in a molar ratio of 1 mole of alkyl thiosulfinyl compound to 1 mole of dithiocarbamate salt preferably at a temperature between about 0° and 200° C. and a pressure of atmospheric to 100 psig for a period of 0.5 to 6 hours. The reaction product thus obtained is purified by filtering, washing and stripping and is then suitable for use as an additive in a lubricating oil. Although I do not wish to be bound by the following structural formula, the resulting product is thought to have the following structure:

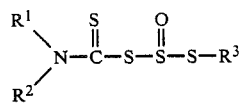

where $R^1$, $R^2$, and $R^3$ are as defined above.

The lubricant compositions hereof may comprise any oleaginous materials that require lubricative properties under extreme pressure conditions and require protection against deterioration by oxidation or by excessive wear under operating conditions. Specially suitable for use with the additives of this invention are liquid hydrocarbon oils of any suitable lubricating viscosity. In general, the lubricant compositions may comprise any mineral or synthetic oil of lubricating viscosity or mixtures thereof. The additives of this invention are especially useful in automotive engine oils, marine diesel oils, aviation lubricants, greases, and in automotive fluids such as brake fluids, power brake fluids, transmission fluids, power steering fluids, various hydraulic fluids and industrial gear oils and in liquid hydrocarbyl fuels.

In instances where synthetic oils are desired in preference to refined petroleum or mineral oil they may be employed alone or in combination with a mineral oil. They may also be used as the vehicle or base of grease compositions. Typical synthetic lubricants include polyisobutylene, polybutenes, hydrogenated polydecenes, polypropylene glycol, polyethylene glycol, trimethylol propane esters, neopentyl and pentaerythritol esters of carboxylic acids, di(2-ethylhexyl) sebacate, di(2-ethylhexyl) adipate, dibutyl phthalate, fluorocarbons, silicate esters, silane, esters of phosphorus-containing acids, liquid ureas, ferrocene derivatives, hydrogenated mineral oils, chain-type polyphenols, siloxanes and silicones (polysiloxanes), alkyl-substituted diphenyl ethers typified by a butyl-substituted bis(p-phenoxy phenyl) ether, phenoxy phenylethers, dialkylbenzenes, etc.

As hereinbefore indicated, the aforementioned additives can be incorporated as additives in grease compositions. When high temperature stability is not a requirement of the finished grease, mineral oils having a viscosity of at least 40 SSU at 150° F. are useful. Otherwise those falling within the range of from about 60 SSU to about 6,000 SSU at 100° F. may be employed. The lubricating compositions of the improved greases of the present invention, containing the above-described additives, are combined with a grease forming quantity of a thickening agent. For this purpose, a wide variety of materials can be dispersed in the lubricating oil in grease-forming qualities in such degree as to impart to the resulting grease composition the desired consistency. Exemplary of the thickening agents that may be employed in the grease formulation are metal soaps as well as non-soap thickeners, such as surface-modified clays and silicas, aryl ureas, calcium complexes and similar materials. In general, grease thickeners are employed which do not melt or dissolve when used at the required temperature within a particular environment; however, in all other respects, any material which is normally employed for thickening or gelling oleaginous fluids or forming greases may be used in the present invention.

Generally the lubricants and fuels of the present invention contain an amount of the product effective to improve extreme pressure properties and antiwear and antioxidation characteristics. Normally this amount will be about 0.01–20%, preferably about 0.01–10%, of the total weight of the lubricant.

The invention also contemplates the use of other additives in combination with the additive of this invention. Such other additives include, for example, detergents and dispersants of the ash-producing or ashless type, corrosion-inhibiting agents, auxiliary oxidation-inhibiting agents, pour point depression agents, auxiliary extreme pressure agents, color stabilizers and antifoam agents.

The folllowing examples serve to illustrate the present invention, but are not intended as limitations thereon unless otherwise stated.

EXAMPLE 1

Preparation of Alkylthiosulfinyl Halide Compounds

Tertiary-nonylthiol, 80 grams (0.5 moles) was added slowly, to an excess (1 mole) of thionyl chloride in a reaction flask isolated from contact with moisture, at a rate sufficient to maintain the exothermic reaction temperature at 35°–40° C., and to control foaming. The excess thionyl chloride was the distilled off. The resulting product is thought to have the structural formula:

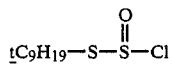

EXAMPLE 2

Preparation of Ammonium Dithiocarbamate Salt

The triethylammonium salt of N,N-di-2-ethylhexyl-dithiocarbamic acid was prepared by reacting bis-2-ethylhexylamine (0.5 moles) and carbon disulfide (0.6 moles) in the presence of triethylamine (0.6 moles) in toluene. This is a reaction well known to those skilled in the art. The product obtained in Example 1 was then added to a stoichiometric amount of this latter triethylammonium salt in 200 milliliters of n-hexane. After this addition, the reaction mixture was refluxed for three hours, cooled and filtered. The filtrate was washed with water dried over MgSO$_4$ and stripped to give 221 grams (85% yield) of dark brown liquid product. The resulting product is thought to have the following structure formula

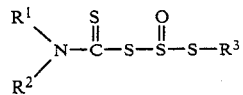

where $R^1$ nd $R^2$ are the same and each R is a 2-ethyl hexyl hydrocarbon radical and $R^3$ is a t-nonyl hydrocarbon radical.

Similar products were prepared utilizing t-hexadecylthiol and t-nonylthiol reacted with thionyl chloride and the resulting product reacted with the triethyl ammonium salt of N,N-bis-2ethylhexyl- and N,N-dibutyl-dithiocarbamic acid.

EVALUATION OF PRODUCT

The additives prepared in Example 2 were blended in a concentration of 1% into a neutral base stock oil and tested for effectiveness as an antioxidant. The blend was tested further in a standard 4-Ball Test Machine for antiwear activity. Test results are shown in Tables 1 and 2 respectively.

The oxidation test reported in Table 1 consists basically of bubbling a stream of air through a volume of the lubricant at the rate of about 5 liters per hour at 325° F. for 40 hours. Present in the composition are samples of metals commonly used in engine construction, namely iron, copper, aluminum and lead. See U.S. Pat. No. 3,682,980, incorporated herein by reference, for further details of the test. Reductions in viscosity index or neutralization number (or both) show effective control.

In the Shell 4-ball wear test for scarring reported in Table 2 S2100 stainless steel balls of ½-inch diameter were used under a 60 Kg load for 30 minutes at 2000 r.p.m. at 200° F. or 300° F.

TABLE 1

| | B-10 Catalytic Oxidation Test 325° F., 40 Hours $R_2NC(S)SS(O)SR^1$ | | |
|---|---|---|---|
| Run | Additive (1%) | % NN Increase | % KV Increase |
| 1 | None | 17.6 | 142.8 |
| 2 | R = C$_8$H$_{17}$ ; R$^1$ = C$_{16}$H$_{33}$-t | 1.3 | 9.8 |
| 3 | R = C$_8$H$_{17}$ ; R$^1$ = C$_9$H$_{19}$-t | 1.8 | 18.1 |
| 4 | R = C$_4$H$_9$ ; R$^1$ = C$_9$H$_{19}$-t | 3.3 | 43.6 |

TABLE 2

| | 4-Ball Wear Test, 2000 rpm ½" Balls, S2100 Steel, 60 kg, 30 Minutes $R_2NC(S)SS(O)SR^1$ | | |
|---|---|---|---|
| Item | Additive (1%) | Wear Scar 200° F. | Diam (mm) 300° F. |
| 1 | None | 2.19 | 2.92 |
| 2 | R = C$_8$H$_{17}$ ; R$^1$ = C$_9$H$_{19}$-t | 0.88 | 1.37 |
| 3 | R = C$_4$H$_9$ ; R$^1$ = C$_9$H$_{19}$-t | 1.14 | 1.23 |
| 4 | R = C$_8$H$_{17}$ ; R$^1$ = C$_{16}$H$_{33}$-t | 1.43 | 1.58 |

I claim:

1. A lubricating composition comprising a major amount of a lubricating oil and between about 0.01 and about 10 percent by weight of the reaction product obtained by reacting an amine or metal dithiocarbamate salt having the following structural formula:

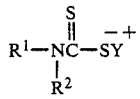

where $R^1$ and $R^2$ are the same or different, each being a hydrocarbyl group containing from 1 to 36 carbon atoms and Y is an ammonium or metal radical with an alkyl thiosulfinyl halide having the structural formula:

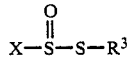

where $R^3$ is an aryl, alkaryl, aralkyl, or a saturated or unsaturated alkyl group and X is halogen.

2. The lubricating composition of claim 1 wherein $R^1$ and $R^2$ have at least one heteroatom which can be oxygen, sulfur, or nitrogen and is selected from the group consisting of alkyl, alkenyl, aryl, aralkyl, alkaryl radicals containing phenyl, naphthyl, or anthryl substituents or are $(CH_n)_m$ comprising part of an alicyclic or heterocyclic system selected from the group consisting of pyrrole, pyrrolidine, morpholine and piperidine, where n is 1 to 2 and m is 2 to 8.

3. The lubricating composition of claim 1 wherein the reactants are reacted in a molar ratio of 1 mole of alkyl thiosulfinyl halide compound to 1 mole of dithiocarbamate salt at a temperature of about 0° C. to about 300° C. and at a pressure of about 0 psig to about 100 psig.

4. The lubricating composition of claim 1 wherein the dithiocarbamate salt is the salt of N,N-di-2-ethylhexyldithiocarbamic acid.

5. The lubricating composition of claim 1 wherein the dithiocarbamate salt is the salt of N,N-dibutyldithiocarbamic acid.

6. The lubricating composition of claim 1 wherein the organo alkyl thiosulfinyl halide is prepared by reacting a thiol compound having a substituent selected from the group consisting of aryl, alkylaryl, and alkaryl, and saturated or unsaturated alkyl groups all with zero or more heteroatoms selected from the group consisting of nitrogen, sulfur, and oxygen with a thionyl halide of the structural formula:

$$SOX_2$$

where X is a halogen.

7. A lubricating composition comprising a major amount of a lubricating oil and between about 0.01 and about 10 percent by weight of the reaction product obtained by reacting an amine or metal salt of N,N-dibutyldithiocarbamic acid with an alkyl thiosulfinyl halide having the structural formula:

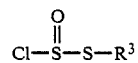

where $R^3$ is an aryl, alkaryl, aralkyl, or a saturated or unsaturated alkyl group.

8. The lubricating composition of claim 1 wherein the lubricating oil is selected from the group consisting of mineral oil, synthetic oil, mixtures thereof, and greases.

9. A method of making a lubricating composition comprising adding to a lubricating oil between about 0.01 and about 10 percent by weight of the reaction product obtained by reacting an amine or metal dithiocarbamate salt having the following structural formula:

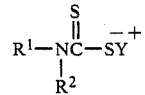

where $R^1$ and $R^2$ are the same or different, each being a hydrocarbyl group containing from 1 to 36 carbon atoms and Y is an ammonium or metal radical with an alkyl thiosulfinyl halide having the structural formula:

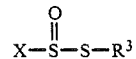

where $R^3$ is an aryl, alkaryl, aralkyl, or a saturated or unsaturated alkyl group and X is halogen.

10. The method of claim 9 wherein $R^1$ and $R^2$ have at least one heteroatom which can be oxygen, sulfur, or nitrogen and is selected from the group consisting of alkyl, alkenyl, aryl, aralkyl, alkaryl radicals containing phenyl, naphthyl, or anthryl substituents or are $(CH_n)_m$ comprising part of an alicyclic or heterocyclic system selected from the group consisting of pyrrole, pyrrolidine, morpholine and piperidine, where n is 1 or 2 and m is 2 to 8.

11. The method of claim 9 wherein the reactants are reacted in a molar ratio of 1 mole of alkyl thiosulfinyl halide compound to 1 mole of dithiocarbamate salt at a temperature of about 0° C. to about 300° C. and at a pressure of about 0 psig to about 100 psig.

12. The method of claim 9 wherein the dithiocarbamate salt is the salt of N,N-di-2-ethylhexyldithiocarbamic acid.

13. The method of claim 9 wherein the dithiocarbamate salt is the salt of N,N-dibutyldithiocarbamic acid.

14. The method of claim 9 wherein the organo alkyl thiosulfinyl halide is prepared by reacting a thiol compound having a substituent selected from the group consisting of aryl, alkaylaryl, and alkaryl, and saturated or unsaturated alkyl groups all with zero or more heteroatom selected from the group consisting of nitrogen, sulfur, and oxygen with a thionyl halide of the structural formula:

$$SOX_2$$

where X is a halogen.

15. The method of claim 9 wherein the reaction product is obtained by reacting an amine or metal salt of N,N-dibutyldithiocarbamic acid with an alkyl thiosulfinyl halide having the structural formula:

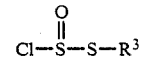

where $R^3$ is an aryl, alkaryl, aralkyl, or a saturated or unsaturated alkyl group.

16. The method of claim 9 wherein the lubricating oil is selected from the group consisting of mineral oil, synthetic oil, mixtures thereof, and greases.

* * * * *